US011813166B2

(12) United States Patent
Hodorek et al.

(10) Patent No.: US 11,813,166 B2
(45) Date of Patent: Nov. 14, 2023

(54) TRIAL RADIAL HEAD IMPLANT

(71) Applicant: Synthes GmbH, Oberdorf (CH)

(72) Inventors: Brian C. Hodorek, Winona Lake, IN (US); Matt J. Purdy, Winona Lake, IN (US); J. Michael Wiater, Beverly Hills, MI (US); Anand M. Murthi, Baltimore, MD (US); Matthew J. Smith, Columbia, MO (US); Derek J. Cuff, Venice, FL (US); Andrew Jawa, Cambridge, MA (US)

(73) Assignee: Synthes GmbH

( * ) Notice: Subject to any disclaimer, the term of this patent is extended or adjusted under 35 U.S.C. 154(b) by 37 days.

(21) Appl. No.: 16/560,221

(22) Filed: Sep. 4, 2019

(65) Prior Publication Data

US 2020/0030105 A1 Jan. 30, 2020

Related U.S. Application Data

(63) Continuation-in-part of application No. 16/025,964, filed on Jul. 2, 2018, now Pat. No. 11,129,719.

(60) Provisional application No. 62/638,844, filed on Mar. 5, 2018.

(51) Int. Cl.
*A61F 2/38* (2006.01)
*A61F 2/30* (2006.01)
*A61F 2/46* (2006.01)

(52) U.S. Cl.
CPC .......... *A61F 2/3804* (2013.01); *A61F 2/4684* (2013.01); *A61F 2002/30112* (2013.01); *A61F 2002/30934* (2013.01); *A61F 2002/3818* (2013.01); *A61F 2002/3827* (2013.01)

(58) Field of Classification Search
CPC .... A61F 2220/0025; A61F 2002/30604; A61F 2002/448; A61F 2/38; A61F 2/3804; A61F 2002/30331; A61F 2002/30341; A61F 2002/30367; A61F 2002/30405; A61F 2002/3809; A61F 2002/3813; A61F 2002/3818; A61F 2002/3827; A61F 2002/4435
See application file for complete search history.

(56) References Cited

U.S. PATENT DOCUMENTS

| | | | |
|---|---|---|---|
| 6,746,487 B2 | 6/2004 | Scifert et al. | |
| 7,648,530 B2 * | 1/2010 | Habermeyer | A61F 2/4003 623/19.13 |
| 7,740,661 B2 | 6/2010 | Baratz et al. | |
| 7,875,082 B2 * | 1/2011 | Naidu | A61F 2/4637 623/20.11 |
| 8,080,063 B2 * | 12/2011 | Ferrand | A61F 2/4081 623/19.13 |
| 8,105,388 B2 * | 1/2012 | Palmer | A61F 2/4261 623/21.12 |
| 8,535,382 B2 | 9/2013 | Kehres et al. | |
| 8,764,845 B2 | 7/2014 | Brooks et al. | |
| 8,840,676 B2 | 9/2014 | Belew et al. | |

(Continued)

FOREIGN PATENT DOCUMENTS

| | | | | |
|---|---|---|---|---|
| EP | 4032506 A1 * | 7/2022 | ........... | A61B 17/025 |
| WO | WO-2011017620 A2 * | 2/2011 | ........... | A61F 2/3804 |

*Primary Examiner* — Ann Schillinger
(74) *Attorney, Agent, or Firm* — BakerHostetler

(57) ABSTRACT

An orthopedic trial implant having a plurality of bearing component augments of differing heights, where each augment releasably, slidably connected to the trial implant.

18 Claims, 13 Drawing Sheets

(56) References Cited

U.S. PATENT DOCUMENTS

| | | |
|---|---|---|
| 8,945,138 B2 | 2/2015 | Klotz et al. |
| 8,998,994 B2 * | 4/2015 | Winslow .............. A61B 17/842 |
| | | 623/19.12 |
| 9,655,726 B2 | 5/2017 | Cooney et al. |
| 9,707,084 B2 | 7/2017 | Huebner et al. |
| 9,746,487 B2 | 8/2017 | Marty et al. |
| 11,129,719 B2 | 9/2021 | Hodorek et al. |
| 2001/0037154 A1 | 11/2001 | Martin |
| 2004/0186580 A1 | 9/2004 | Steinmann |
| 2005/0075735 A1 | 4/2005 | Berelsman et al. |
| 2005/0216090 A1 | 9/2005 | O'Driscoll et al. |
| 2008/0288079 A1 | 11/2008 | Leibel |
| 2009/0132045 A1 | 5/2009 | Lafosse |
| 2009/0149960 A1 | 6/2009 | Hushka et al. |
| 2009/0240336 A1 | 9/2009 | Vander et al. |
| 2009/0319050 A1 | 12/2009 | Palmer et al. |
| 2010/0241236 A1 | 9/2010 | Katrana et al. |
| 2012/0078376 A1 * | 3/2012 | Vanasse ................ A61F 2/4261 |
| | | 623/21.12 |
| 2012/0083892 A1 * | 4/2012 | Kehres ................ A61F 2/3804 |
| | | 623/20.11 |
| 2012/0179263 A1 * | 7/2012 | Metcalfe ................... A61F 2/40 |
| | | 623/19.14 |
| 2013/0150972 A1 * | 6/2013 | Iannotti ................ A61F 2/4059 |
| | | 623/18.11 |
| 2014/0012388 A1 * | 1/2014 | Brownhill ............. A61F 2/3804 |
| | | 623/20.13 |
| 2014/0074246 A1 | 3/2014 | Huebner et al. |
| 2014/0303742 A1 | 10/2014 | Prybyla et al. |
| 2015/0250602 A1 * | 9/2015 | Sikora .................. A61F 2/4637 |
| | | 623/19.12 |
| 2016/0051365 A1 | 2/2016 | Brownhill et al. |
| 2017/0095338 A1 | 4/2017 | Bergquist et al. |
| 2017/0340449 A1 * | 11/2017 | Deransart ............. A61F 2/4014 |
| 2022/0023054 A1 * | 1/2022 | Hatzidakis ............ A61B 17/68 |

* cited by examiner

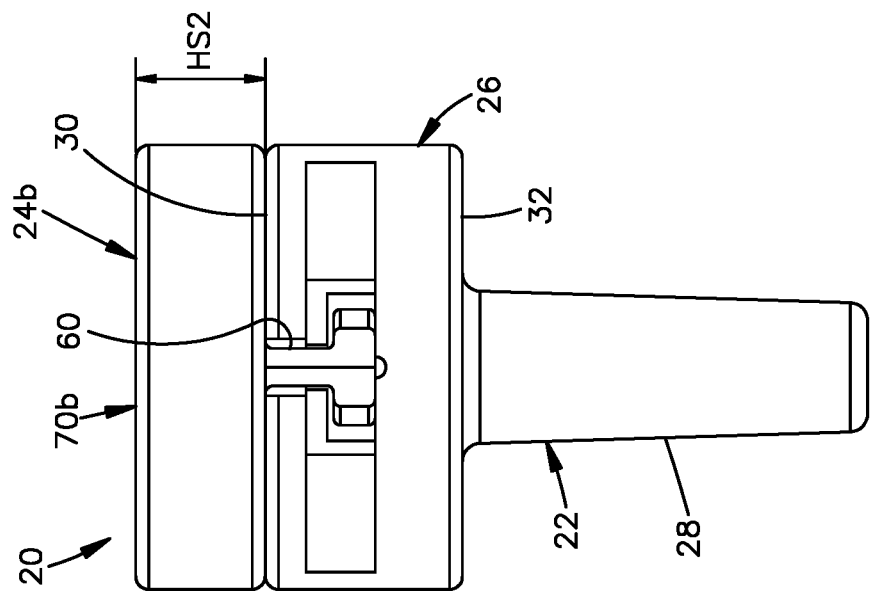
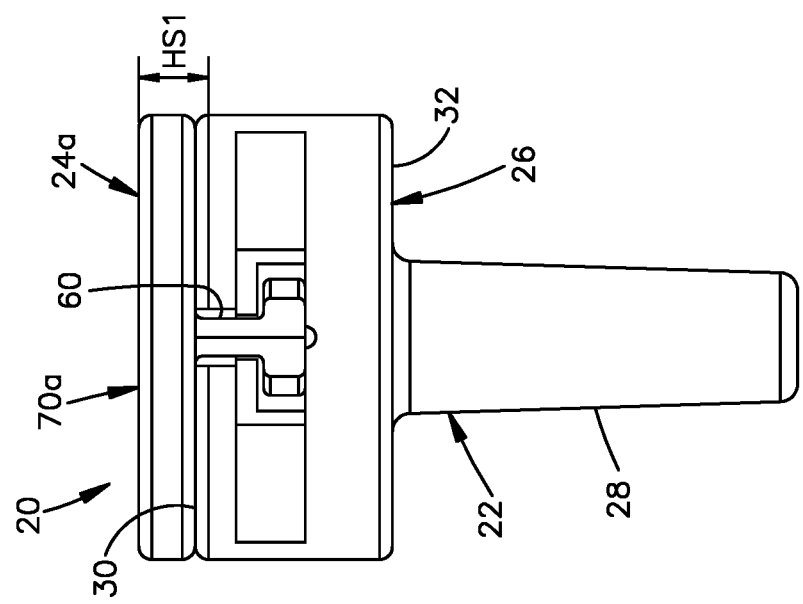
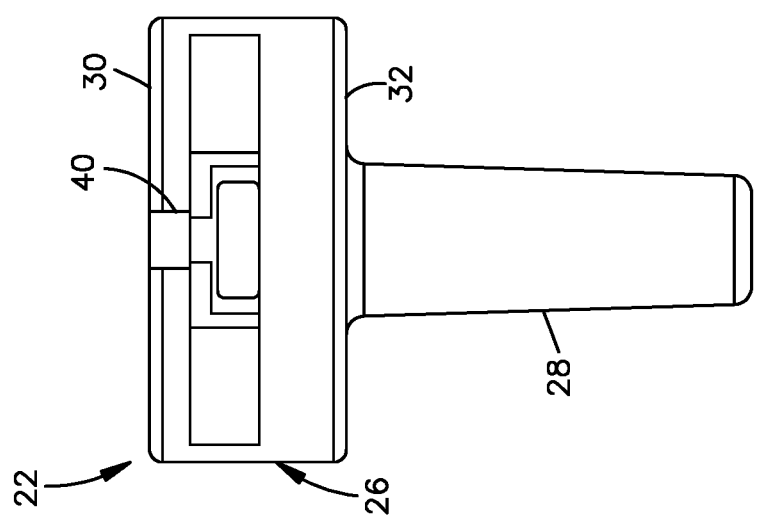

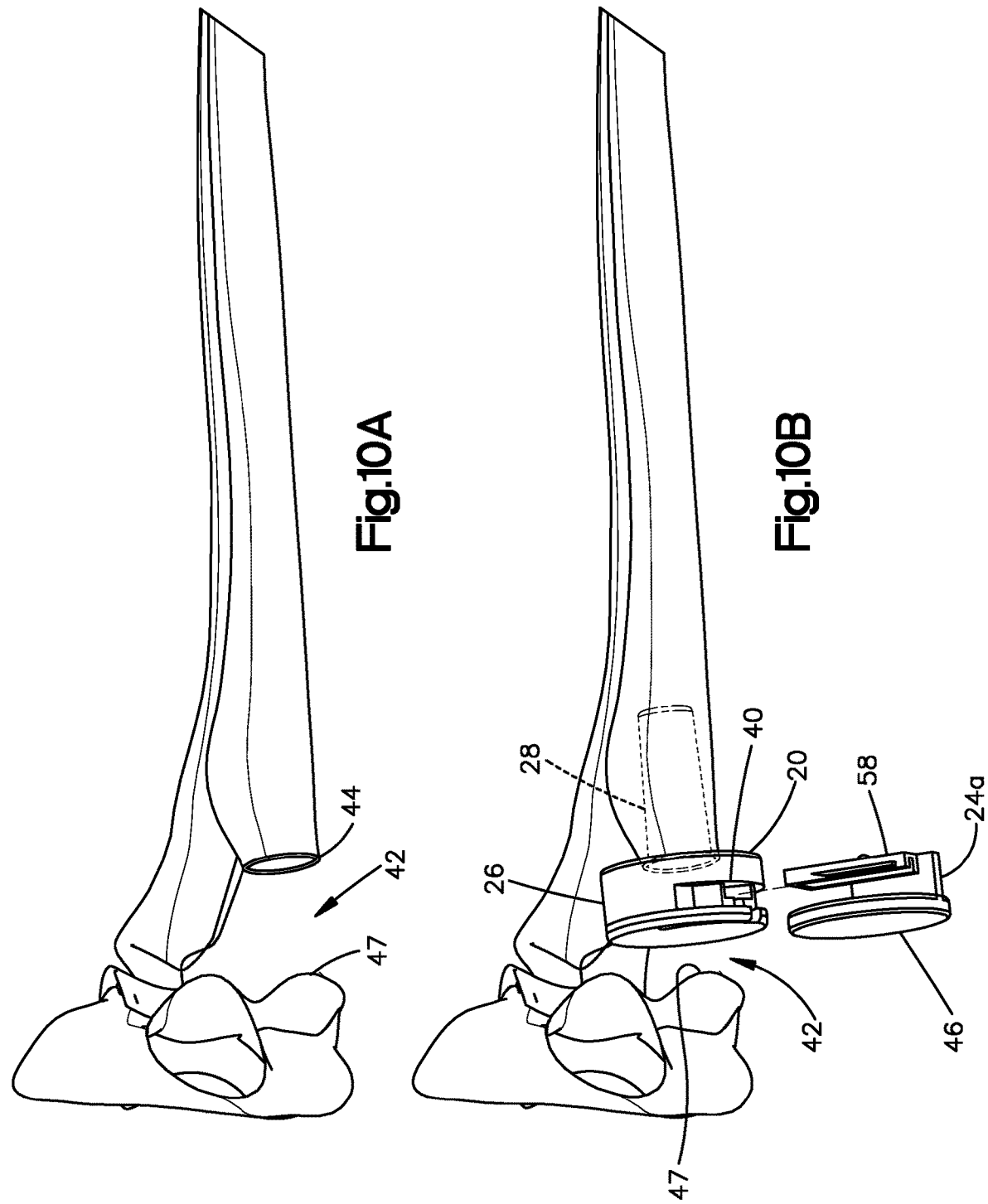

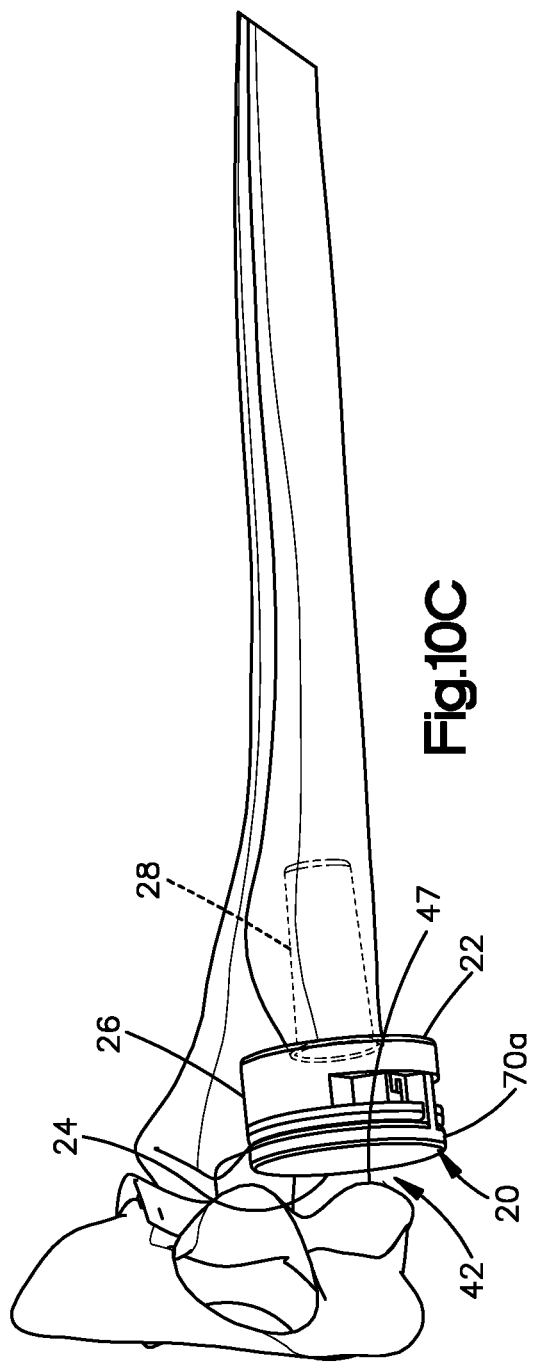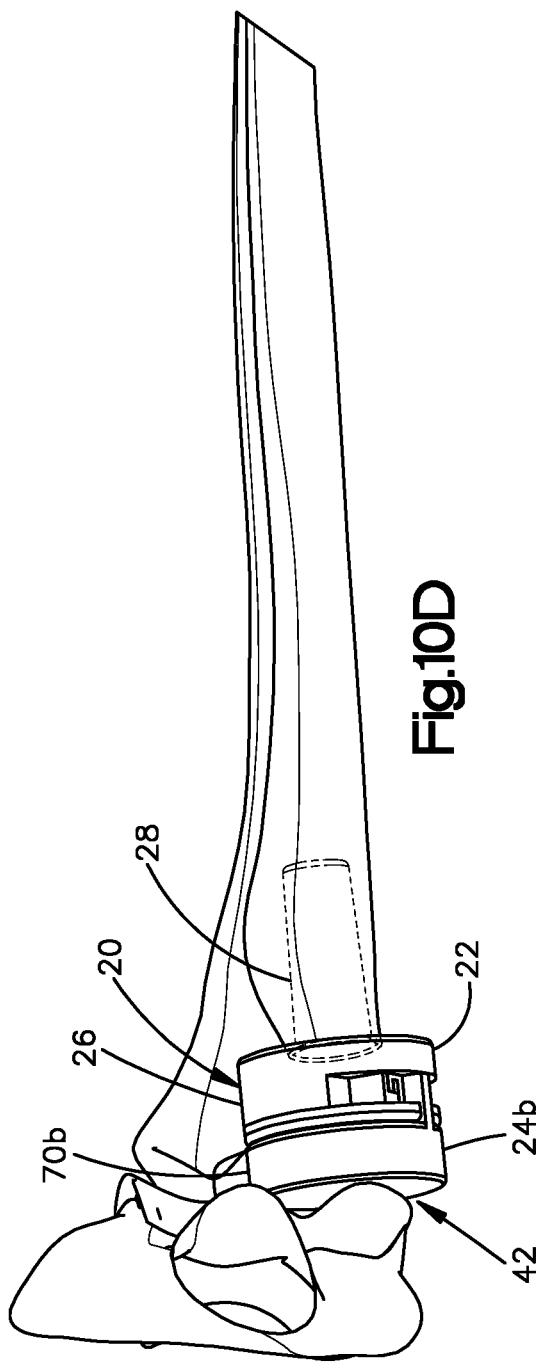

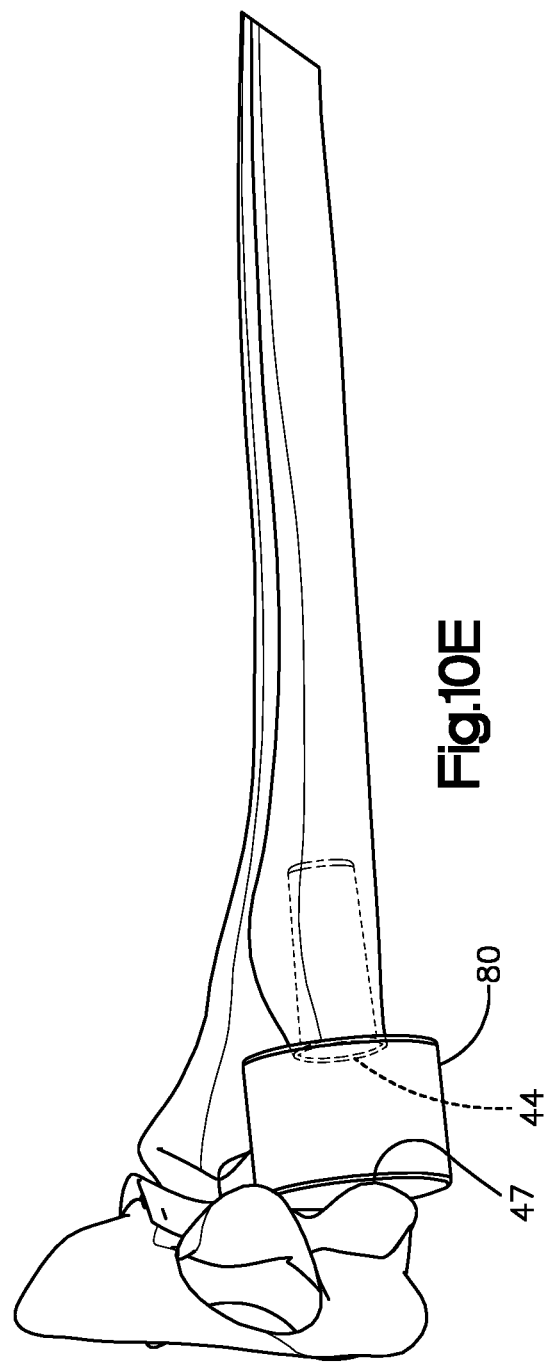

TRIAL RADIAL HEAD IMPLANT

CROSS-REFERENCE TO RELATED APPLICATIONS

This is a continuation-in-part of U.S. patent application Ser. No. 16/025,964 filed Jul. 2, 2018, which in turn claims priority to U.S. patent application Ser. No. 62/638,844 filed Mar. 5, 2018, the disclosure of each of which is hereby incorporated by reference as if set forth in its entirety.

BACKGROUND

1. Technical Field

The present invention relates generally to trial orthopedic implant devices and systems and, more particularly to trial orthopedic implant devices and systems for determining the height of a final radial head implant.

2. Description of the Related Art

Some fractures of the radius occur in the part of the bone that is proximate the elbow, called the radial "head". Radial head fractures are common injuries that may result from an acute elbow injury. Fractures of the radial head are typically treated with a variety of surgical and non-surgical options depending upon the severity of the injury. For example, surgical options for more severe injuries to the radial head can include open reduction with internal fixation (ORIF), radial head resection, hemi-arthroplasty (e.g., radial head arthroplasty), and total arthroplasty (i.e., total elbow replacement).

Radial head arthroplasty involves resecting the fractured and damaged radial head and replacing the natural articulation surface with an artificial articulation surface of an implant. The articulating surface of the implant articulates with the natural cartilage surface of the capitellum of the distal humerus.

In radial head replacement procedures, a radial head prosthesis is implanted into the medullary canal of the proximal radius. The radial head may cooperate with an ulna or ulnar prosthesis to provide radioulnar joint articulation. The radial head may cooperate with a humerus or humeral prosthesis to provide radiohumeral joint articulation.

Prior to implantation of a radial head implant, a surgeon selects an implant having a size that properly fits the implant site of the particular patient. Many known systems include trial stems and trial heads the surgeon can assemble and use prior to final implantation to evaluate the fit for selecting the most appropriately sized implant. However, known systems do not offer a simple effective means for trying a plurality of different humeral head heights to determine the proper height for a final radial head implant. Exemplary systems include the following prior art devices:

U.S. Pat. No. 6,746,487 discloses an intramedullary fixation device for use in securing a trial in the medullary canal of a bone to determine the offset and orientation of a prosthetic implant for replacement of a joint articulating surface of the bone is disclosed. The fixation device comprises a body for receiving a trial and a fixation portion for engaging the trial. A system for use in surgical repair of a joint comprising a selection of prosthetic implants of various sizes, a selection of trials of various sizes corresponding to the sizes of the implants, a selection of fixation devices of various sizes corresponding to the sizes of the trials, a trial fixation device driver for inserting the fixation device and attached trial into the canal of a bone, and a trial device extractor for removing the fixation device from the resected bone is disclosed, Methods of using the fixation device and system of the invention are disclosed.

U.S. Pat. No. 7,740,661 discloses radial head implant apparatuses and methods. In one embodiment, a radial head implant can include a head portion for articular engagement with a humerus bone, a stem portion for engagement with a radius bone, and a shaft for engagement with the stem portion. The head portion can include an upper surface for engaging the humerus bone. The stem portion can have an axial opening for receiving at least a portion of the shaft, and a collar can be disposed around the stem portion at a proximal end thereof. An upper portion of the shaft can be configured for engaging the head portion, while a distal portion of the shaft can be elongated and cylindrical for axially fitting into and moving within the axial opening of the stem portion. Other embodiments are also disclosed for axial movement for a radial head implant. Various structures are disclosed for locking the shaft in position within the stem portion.

U.S. Pat. No. 8,535,382 discloses a prosthesis system for replacement of a head portion of a proximal radius. The system can include a first polymeric articulation component having a first locking portion and a metal head component having a second locking portion. The second locking portion can mate with the first locking portion to form a first locking mechanism to initially couple the first articulation component to the head component. The head component can define a locking channel. The system can also include a stem component having a protrusion receivable in the locking channel. The protrusion can define a bore, and the stem component can be adapted to be coupled to the radius. The system can also include a fastener received through the locking channel and into the bore to provide a second locking mechanism that couples the head component to the stem component.

U.S. Pat. No. 8,764,845 discloses a kit for use in a procedure for implantation of an orthopaedic joint prosthesis includes a head component of an orthopaedic joint prosthesis, which comprises a body part having a convex bearing surface, and a reverse face at which the head component can be connected to a mating component of the joint prosthesis, in which the head component has a chamfer surface extending around at least part of its periphery where the bearing and reverse faces come together, and a plurality of markings on the chamfer surface. The kit includes a trial head component which comprises a body part having a convex trial bearing surface and a reverse face, in which the trial head component has a plurality of markings on the trial bearing surface at or towards the interface between it and the reverse face. The transverse dimensions of the head component are approximately the same as the transverse dimensions of the trial head component, and in which the location of the markings on the chamfer surface around the periphery of the head component corresponds to the location of the markings on the trial bearing surface of the trial head component around its periphery.

U.S. Pat. No. 8,840,676 discloses a prosthesis trial system includes at least one head member having an outer surface and a cavity configured to mate with an exterior surface of a stem member. The prosthesis trial system further includes at least one shell member having an inner surface configured to mate with the outer surface of the at least one head member.

U.S. Pat. No. 8,945,138 discloses a kit for use in performing a trial reduction in joint arthroplasty is provided.

The kit includes a trial stem assembly including a first component, a second component selectably moveable with respect to the first component, and a fastener for securing the first component to the second component. The kit also includes an articulating trial component removeably fixedly secured to the trail stem assembly and a driver for cooperation with the fastener to secure the first component to the second component. The kit also includes a handle. The handle has a first feature for permitting the driver to pass through the handle and a second feature for orientably connecting the handle to the articulating trial component.

U.S. patent application publication no. 20040186.580 discloses a radial head replacement system includes a radial head replacement, an apparatus for guiding the resection of a radial head, and a kit including bone plug and bone plug insertion instrument. The radial head replacement has a separate adjustable head portion that may be secured on an implanted stem such that the implanted radial head replacement smoothly interfaces with the capitellum of the humerus. In another form, the radial head replacement uses crossed bone screws that serve to more securely anchor the stem of the radial head replacement in the medullary canal of the radius. The resection guide includes a movable cutting guide which ensures a precise resection of the radial head and thereby allows for better positioning of the implanted radial head replacement. The bone plug limits the travel of bone cement beyond the area of affixation of the stem portion of a radial head replacement to the radius.

U.S. patent application publication no. 20050075735 discloses a modular prosthesis system for replacement of a head portion of a radius. The prosthesis system includes a head component having a first connection portion that connects to a second connection portion and a collar component having the second connection portion and a third connection portion. The system also includes a stem component including a fourth connection portion that connects with the third connection portion, the stem component having a stem anchoring portion that connects to the radius. The collar component provides the modular geometry to the prosthesis without having to have an increased number of head components and stem components with variable lengths and angles.

U.S. patent application publication no. 2016005!365 discloses a radial head trial device for replacement of a proximal radial head includes a stem component having a center longitudinal axis extending between a proximal end and a distal end, a head component axially and removably attachable to the stem component, wherein the head component is interchangeable with a selection of other head components each axially and removably attachable to the stein component, an anti-rotation feature, and a recess, wherein the anti-rotation feature is structured to be received in the recess to prohibit rotation of the head component relative to the stem component.

What is needed in the art is a trial radial head implant device and system that allows less joint distraction and a simpler device for confirming final implant height.

SUMMARY

In accordance with one example of the present disclosure, an orthopedic trial implant assembly can include at least one radial trial implant and at least one spacer. The radial trial implant can include a head body that defines a proximal head body surface and a distal head body surface opposite the proximal head body surface substantially along a longitudinal direction. The head body can have a height that extends from the proximal head body surface to the distal head body surface along the longitudinal direction. The radial trial implant can further include a stem that extends from the head body along a distal direction that is substantially defined by the longitudinal direction. The at least one spacer can be configured to removably attach to the radial trial implant along a direction substantially perpendicular to the longitudinal direction so as to define a composite head including the head body and a spacer head of the spacer. The composite head defines a proximal composite head surface and a distal composite head surface opposite the proximal composite head surface along the longitudinal direction, and the composite head defines a composite head height from the proximal composite head surface to the distal composite head surface. One of the proximal composite head surface and the distal composite head surface can be defined by the head body, and the other of the proximal composite head surface and the distal composite head surface can be defined by the spacer head. In one example, the composite head height is greater than the head body height.

BRIEF DESCRIPTION OF THE DRAWINGS

The following detailed description will be better understood when read in conjunction with the appended drawings, in which there is shown in the drawings example embodiments for the purposes of illustration. It should be understood, however, that the present disclosure is not limited to the precise arrangements and instrumentalities shown. In the drawings:

FIG. 9A is a side elevation view of the radial trial implant illustrated in FIG. 1;

FIG. 9B is a side elevation view of an orthopedic trial implant assembly including the radial trial implant illustrated in FIG. 9A, and a first spacer attached to the radial trial implant;

FIG. 9C is a side elevation view of an orthopedic trial implant assembly including the radial trial implant illustrated in FIG. 9A, and a second spacer attached to the radial trial implant, wherein the second spacer has a different height than the first spacer illustrated in FIG. 9B;

FIG. 10A shows a proximal radius prepared to receive the radial trial implant;

FIG. 10B shows a radial trial implant that has been implanted in the proximal radius, further showing a first spacer configured to attach to the implanted radial trial implant;

FIG. 10C shows an orthopedic trial assembly implanted in the proximal radial radius, showing the first spacer attached to the radial trial implant;

FIG. 10D shows an orthopedic trial implant assembly implanted in the proximal radius as illustrated in FIG. 10C, but whereby the first spacer has been removed and a second spacer has been attached to the radial trial implant;

FIG. 10E shows a final radial implant that has been implanted in the proximal radius.

Corresponding reference characters indicate corresponding parts throughout the several views. The exemplary embodiments set forth herein are not to be construed as limiting the scope of the invention in any manner.

DETAILED DESCRIPTION

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all of the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
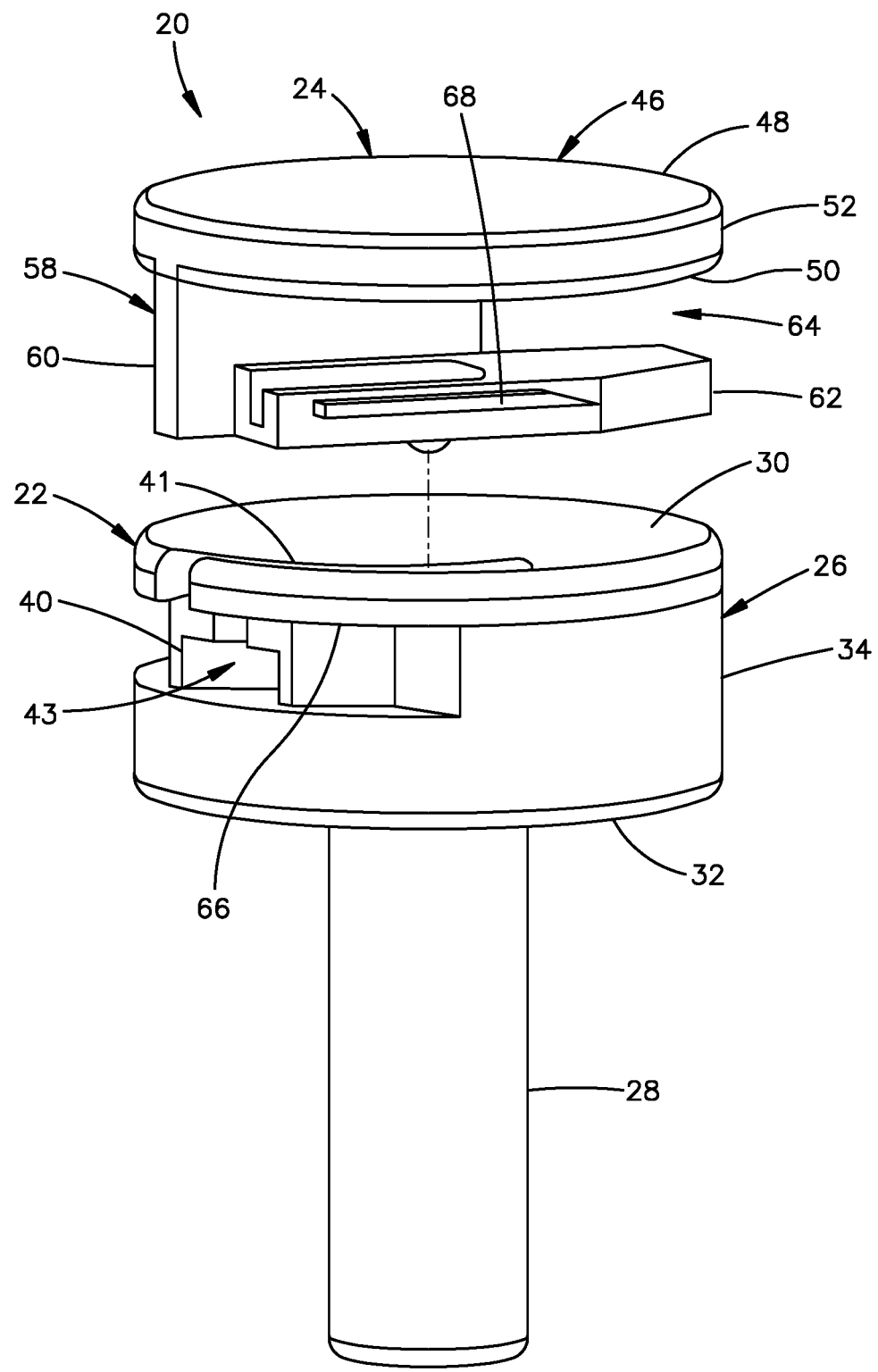
FIG. 1 is a perspective exploded view of an orthopedic trial implant assembly including a radial trial implant and a spacer configured to be releasably attached to the radial trial implant.
Figure 2:
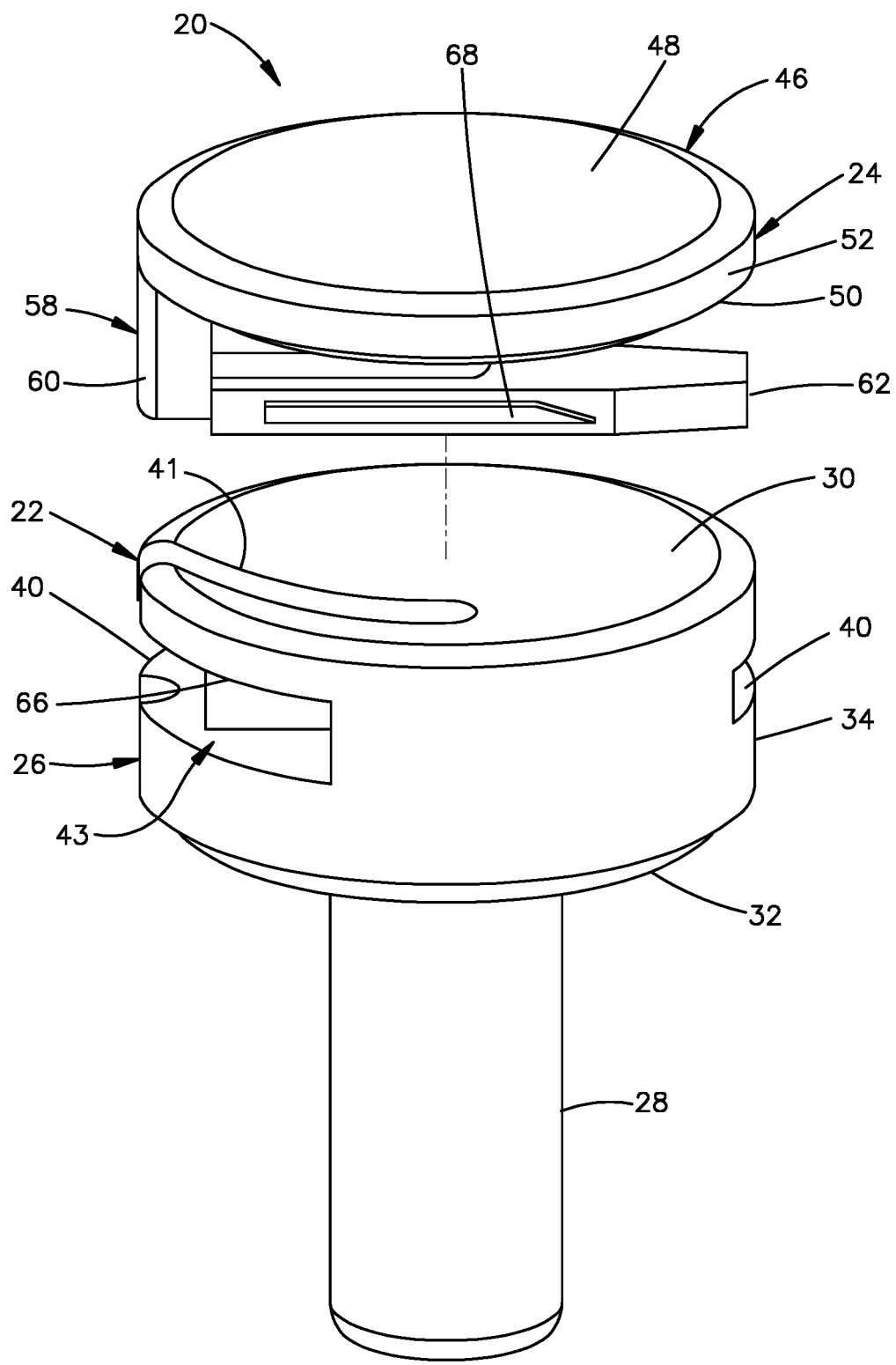
FIG. 2 is another perspective exploded view of the orthopedic trial implant assembly illustrated in FIG. 1.
Figure 3:
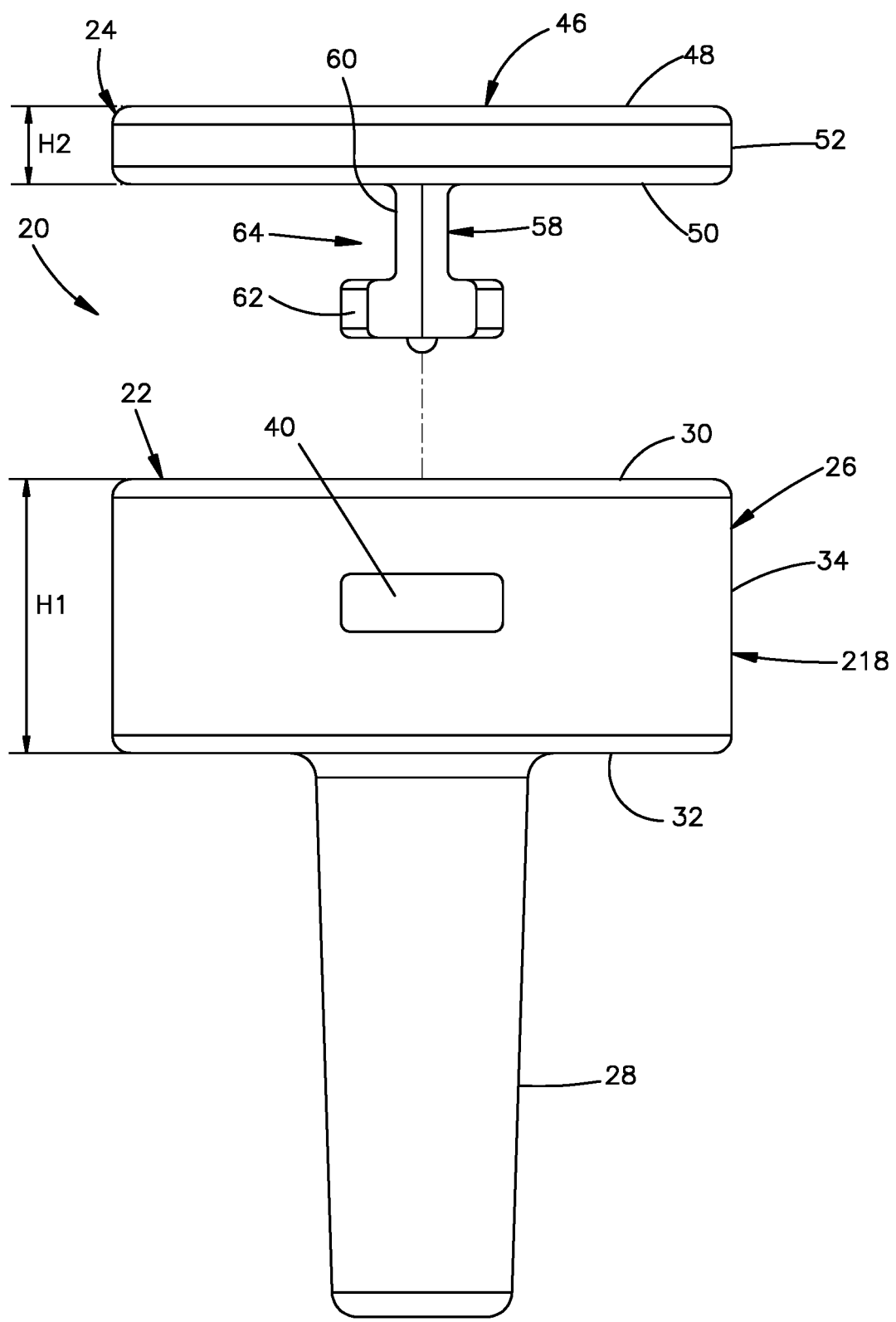
FIG. 3 is an exploded elevation view of the orthopedic trial implant assembly illustrated in FIG. 1.

Referring now to FIGS. 1-3, an orthopedic trial implant assembly 20 can be configured as a radial trial implant assembly configured to be implanted in the proximal radius. The orthopedic trial implant assembly 20 includes a radial trial implant 22 and a radial trial spacer 24 that is configured to be removably attached to the radial trial implant 22. The radial trial implant 22 and the radial trial spacer 24 can be made of any suitable plastic or other suitable material.

As illustrated in FIGS. 1-4A, the radial trial implant 22 includes a head body 26 and a stein 28 that extends out from the head body 26. In one example, the stem 28 can be monolithic with the head body 26. Alternatively, the stein 28 can be separate from the head body 26 and attached to the head body 26.

The head body 26 defines a proximal head body surface 30 and a distal head body surface 32 that is opposite the proximal head body surface 30 substantially along a longitudinal direction. For instance, the distal head body surface 32 is spaced from the proximal head body surface 30 in a distal direction that is defined by the longitudinal direction. Conversely, the proximal head body surface 30 is spaced from the distal head body surface 32 in a proximal direction that is opposite the distal direction and defined by the longitudinal direction. Thus, the term "distal," "distally," and derivatives thereof as used herein refer to a direction from the proximal head body surface 30 to the distal head body surface 32. The term "proximal," "proximal," and derivatives thereof as used herein refer to a direction from the distal head body surface 32 to the proximal head body surface 30.

The term "substantially" and "approximate" and derivatives thereof as used herein recognizes that the referenced dimensions, sizes, shapes, directions, or other parameters can include the stated dimensions, sizes, shapes, directions, or other parameters and up to ±20%, including ±10%, ±5%, and ±2% of the stated dimensions, sizes, shapes, directions, or other parameters.

In one example, the proximal head body surface 30 can define an articular surface that can be configured to cooperate with an ulna or ulnar prosthesis to provide radioulnar joint articulation. The proximal head body surface 30 can cooperate with a humerus or humeral prosthesis to provide radiohumeral joint articulation. In this regard, the proximal head body surface 30 can be a concave surface. The distal head body surface 32 can be a substantially flat surface. It should be appreciated, of course, that the proximal head body surface 30 and the distal head body surface 32 can be shaped in any suitable manner as desired. The stem 28 can extend out from the distal head body surface 32 along the distal direction.

Figure 4A:
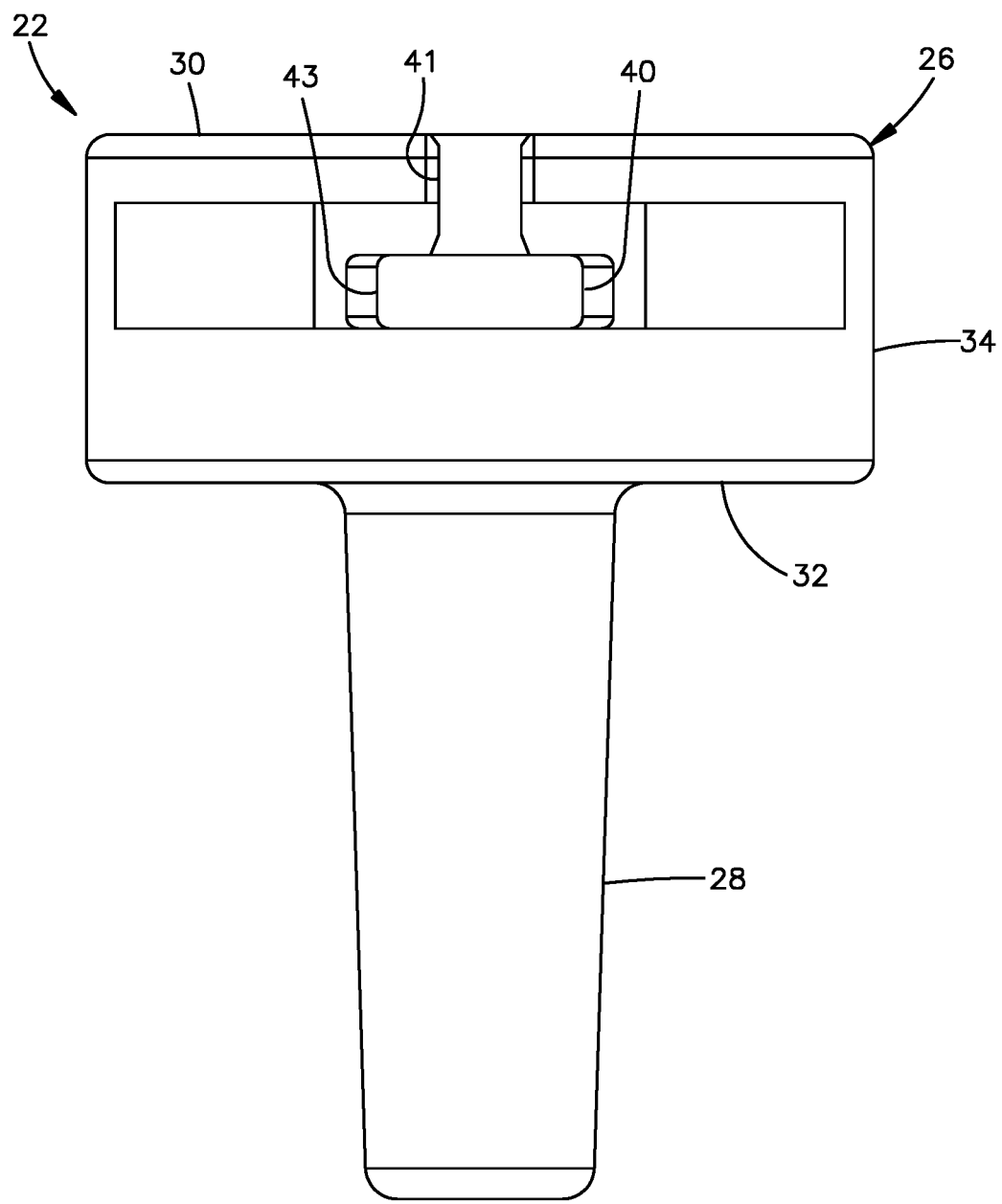
FIG. 4A is a side elevation view of the radial trial implant illustrated in FIG. 1.
Figure 4B:
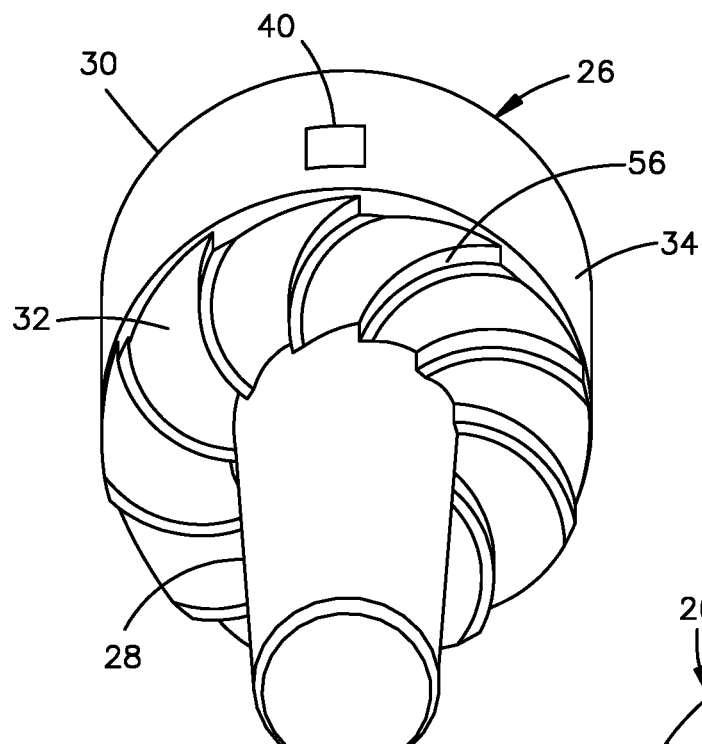
FIG. 4B is a perspective view of a head body of the radial trial implant illustrated in FIG. 4A, but including cutting teeth in one example.
Figure 4C:
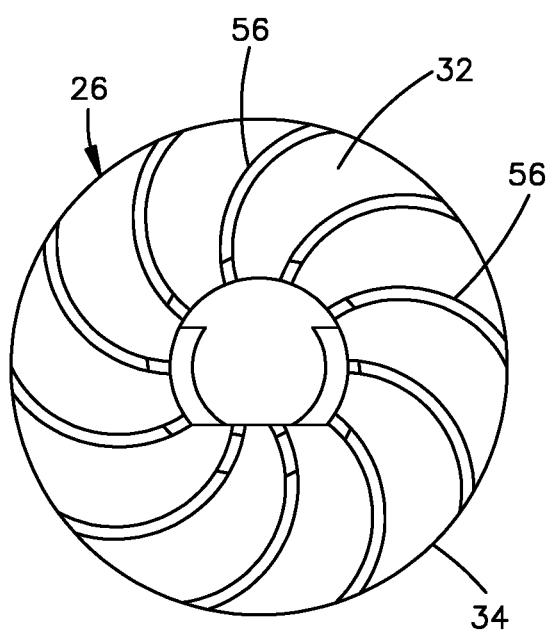
FIG. 4C is a bottom plan view of a head body of the radial trial implant illustrated in FIG. 4A, showing the cutting teeth having a curved shape.
Figure 4D:
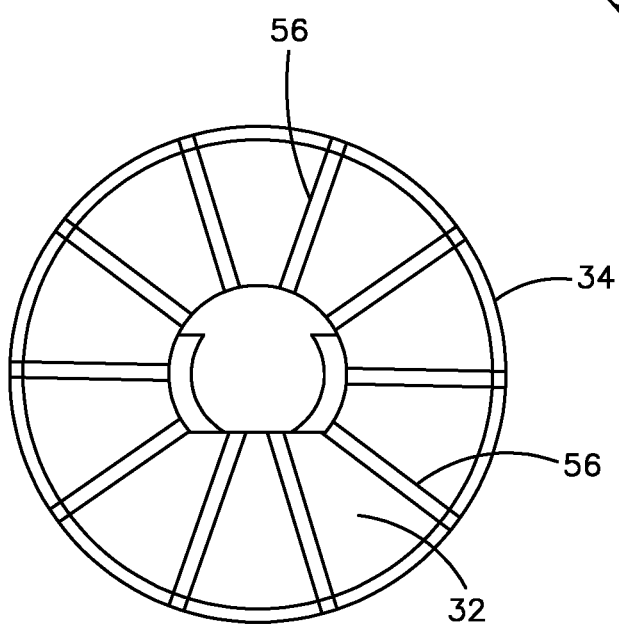
FIG. 4D is a bottom plan view of the head body similar to FIG. 4C, but wherein the cutting teeth are straight and linear.
Figure 5:
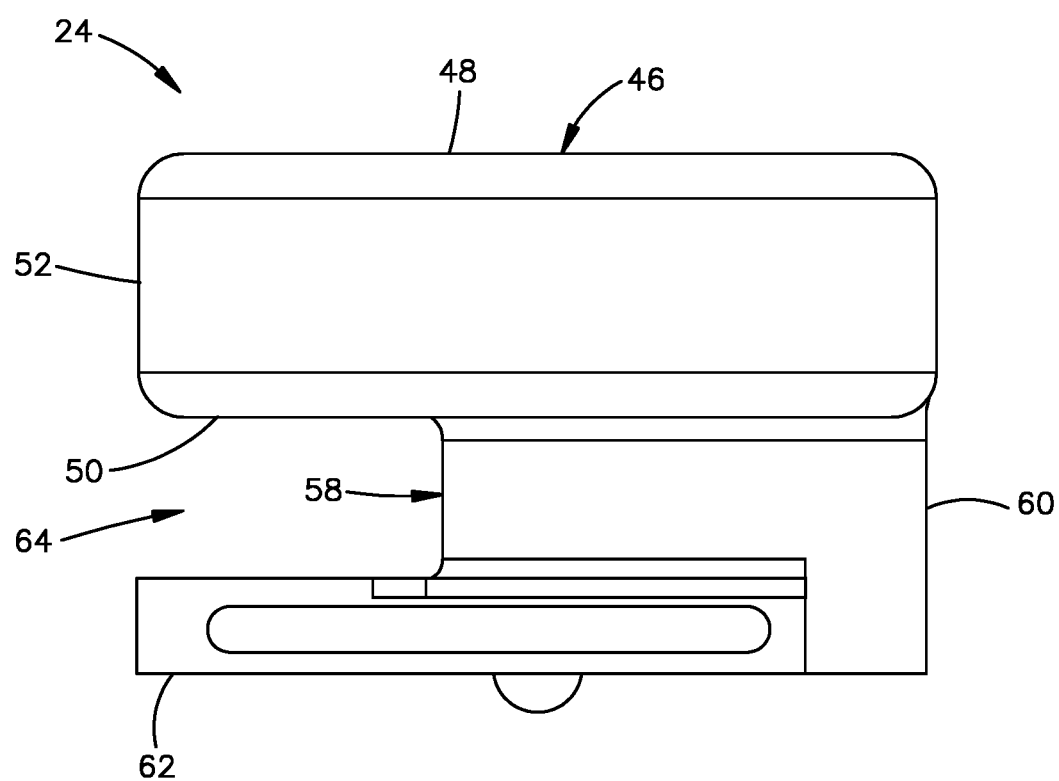
FIG. 5 is a side elevation view of a trial spacer configured to be attached to the radial trial implant illustrated in FIG. 4A.
Figure 6:
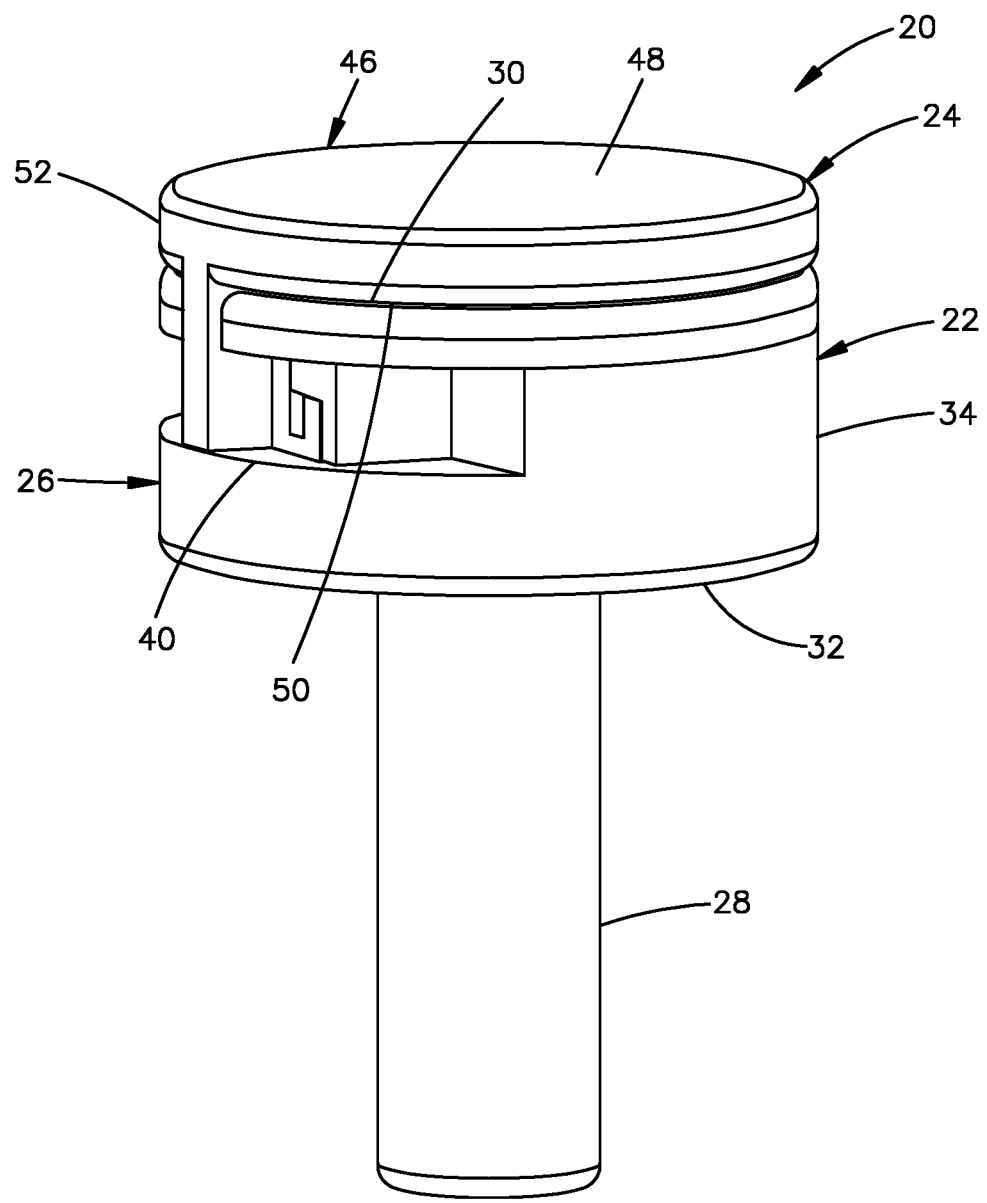
FIG. 6 is a perspective view of the orthopedic trial implant assembly illustrated in FIG. 1, showing the radial trial implant removably attached to the radial trial implant.

In one example, the distal head body surface 32 can be substantially smooth. Alternatively, as illustrated in FIGS. 4B-4D, the distal head body surface 32 can define a plurality of cutting teeth 56 that are configured to planarize the radius as the head body 26 is rotated about its central axis that is oriented along the longitudinal direction. The cutting teeth 56 can extend distally, and can be monolithic with the distal head body surface 32. Alternatively, the cutting teeth 56 can be separate from the radial trial implant 22 and attached to the distal head body surface 32. The cutting teeth 56 can be circumferentially arranged about the distal head body surface 32. In one example shown in FIGS. 4B-4C, the teeth can be shaped as segments of swept spirals. Thus, the teeth 56 can be referred to as swept spiral teeth. Alternatively, as illustrated in FIG. 4D, the cutting teeth 56 can be are oriented straight and linear. Further, the cutting teeth 56 can be oriented radially as they extend about the distal head body surface 32. In one example, the cutting teeth 56 can intersect each other at the central axis of the head body 26.

Referring again to FIGS. 1-4A, the head body 26 can further include at least one side wall 34 that extends from the proximal head body surface 30 to the distal head body surface 32. The at least one side wall can define an outer perimeter of the head body 26 in a plane that is oriented perpendicular to the longitudinal direction. The at least one side wall 34 can be configured as a single substantially cylindrical side wall 34. The cylindrical side wall 34 can extend along a central axis that is oriented along the longitudinal direction. Alternatively, the at least one side wall 34 can be defined by a plurality of connected walls that define the outer perimeter of the head body 26. Further, the side wall 34 can be substantially flat along the longitudinal direction from the proximal head body surface 30 to the distal head body surface 32. As will be described in more detail below, the head body 26 can define a channel 40 that extends into the at least one side wall 34 that is configured to receive the spacer 24 so as to removably attach the spacer 24 to the radial trial implant 22.

The head body 26 defines a height H1 that extends from the proximal head body surface 30 to the distal head body surface 32 substantially along the longitudinal direction. It is envisioned that the height H1 of the head body 26 may be less than the gap 42 between the proximal radius 44 (see FIG. 10A) and a complementary articulating surface 47 that can be defined by one or both of the ulna and humerus. In such instances, it may be desirable to attach the spacer 24 to the radial trial implant 22 so as to increase the height of the head body 26.

Referring now to FIGS. 1-3 and 5, the spacer 24 includes a spacer head 46 that includes a proximal spacer head surface 48 and a distal spacer head surface 50 that is opposite the proximal spacer head surface 48 and spaced from the proximal spacer head surface 48 along the distal direction. In one example, the proximal spacer head surface 48 can define an articular surface that can be configured to cooperate with an ulna or ulnar prosthesis to provide radio-ulnar joint articulation. The proximal spacer head surface 48 can cooperate with a humerus or humeral prosthesis to provide radiohumeral joint articulation. In this regard, the proximal spacer head surface 48 can be a concave surface. The distal spacer head surface 50 can be a substantially convex surface. Accordingly, the distal spacer head surface 50 can be configured to nest with the proximal head body surface 30 when the spacer 24 is attached to the radial trial implant 22. It should be appreciated, of course, that the proximal spacer head surface 48 and the distal spacer head surface 50 can be shaped in any suitable manner as desired.

The spacer 24 can further include at least one side wall 52 that extends from the proximal spacer head surface 48 to the distal spacer head surface 50. The at least one side wall 52 can define an outer perimeter of the spacer head 46 in a plane that is oriented perpendicular to the longitudinal direction. The at least one side wall 52 can be configured as a single substantially cylindrical side wall 52. The cylindrical side wall 52 can extend along a central axis that is oriented along the longitudinal direction. The central axis of the cylindrical side wall 52 of the spacer can be parallel with or coincident with the central axis of the cylindrical side wall 34 of the trial radial prosthesis 22. Alternatively, the at least one side wall 52 can be defined by a plurality of connected walls that define the outer perimeter of the spacer head 46. Further, the side wall 52 can be substantially flat along the longitudinal direction from the proximal spacer head surface 48 to the distal spacer head surface 50.

Figure 7:
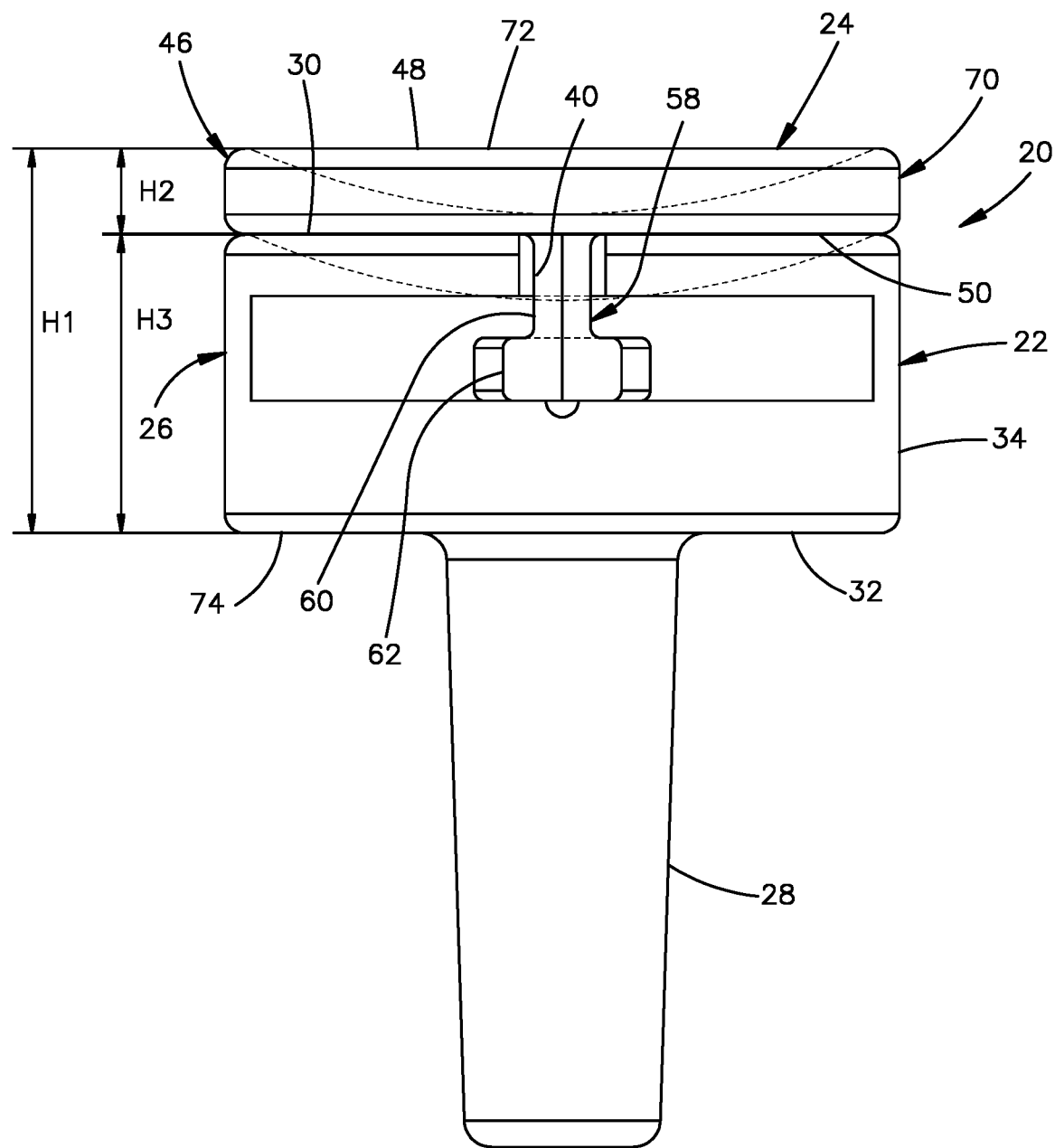
FIG. 7 is a schematic side elevation view of the orthopedic trial implant assembly illustrated in FIG. 1, showing the radial trial implant attached to the spacer.
Figure 8:
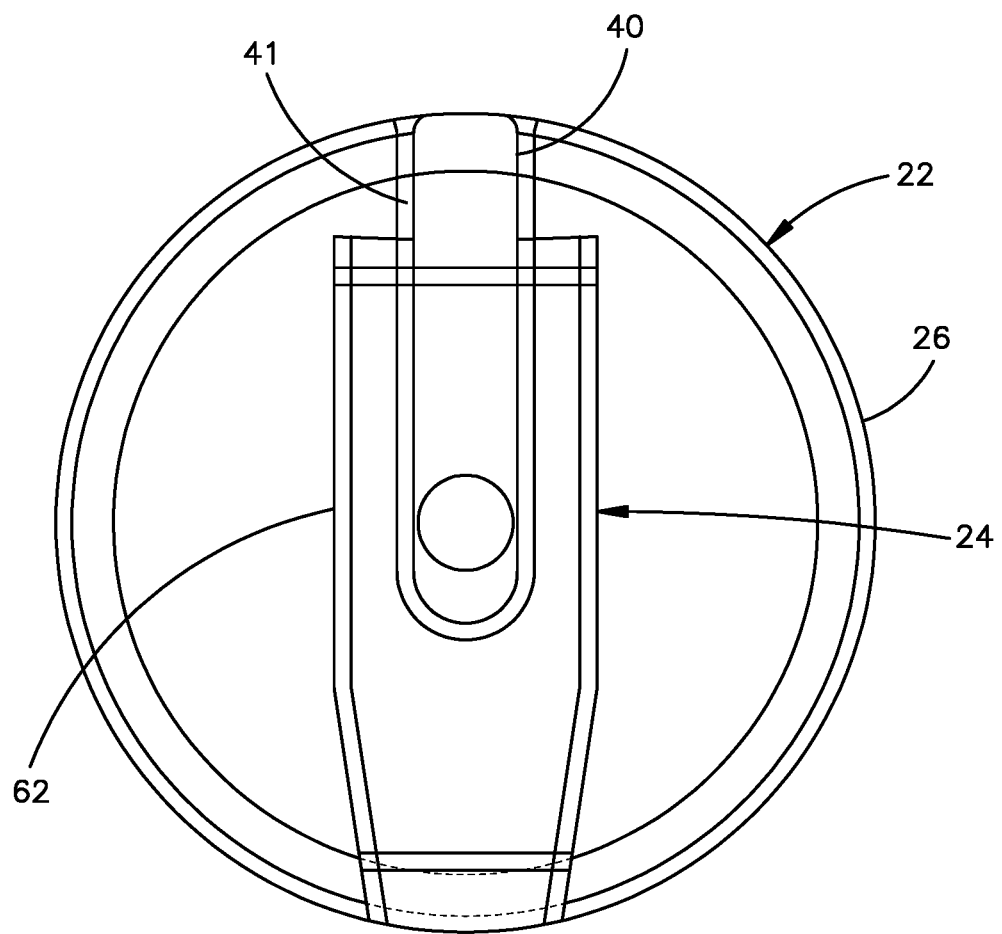
FIG. 8 is a schematic plan view of the orthopedic trial implant assembly illustrated in FIG. 1, showing the radial trial implant attached to the spacer.

The spacer head 46 defines a spacer head height H2 that extends from the proximal spacer head surface 48 to the distal spacer head surface 50 substantially along the longitudinal direction. It is envisioned that the spacer head height H2 can be less than the height H1 of the head body 26. The spacer 24 is configured to be removably attached to the radial trial implant 22 such that the spacer head 46 and the head body 26 define a composite head 54 having a composite head height H3 (see FIG. 7) that is greater than the height H1 of the head body 26. For instance, the composite head height H3 can be substantially equal to the sum of the height H1 of the head body 26 and the spacer head height H2, as shown in FIG. 7.

With continuing reference to FIGS. 1-3 and 5, the spacer 24 can include an attachment member 58 that is configured to attach to a complementary attachment member of the radial trial implant 22. In particular, the complementary attachment member of the radial trial implant 22 can be configured as the channels 40. The attachment member 58 of the spacer 24 can be received in the channel 40 so as to attach the spacer 24 to the radial trial implant 22. In other examples, it is envisioned that the attachment member of the radial trial implant 22 can be received in a channel of the spacer 24 so as to removably attach the spacer 24 to the radial trial implant 22.

Referring now to FIGS. 1-8 generally, the attachment member 58 can include an extension member 60 that extends from the spacer head 46. In particular, the extension member 60 can extend substantially distally from the spacer head 46. In one example, the extension member 60 can extend substantially distally from the distal spacer head surface 50. Thus, the extension member 60 can have a first end that extends out from the distal spacer head surface 50, and the extension member 60 can extend from the first end to a second end substantially along the longitudinal direction. The extension member 60 is sized to be received in a proximal portion 41 of the channel 40 that can be open to the proximal head body surface 30. In particular, the channel 40 can extend through the proximal head body surface 30 along the proximal direction.

The attachment member 58 can further include an attachment tab 62 that extends from the extension member 60. In particular, the attachment tab 62 can extend out from the extension member 60 along a first direction that is substantially perpendicular to the longitudinal direction. For instance, the attachment tab 62 can extend out from the second end of the extension member. The attachment tab 62 is configured to be slidingly inserted into a distal portion 43 of the channel 40 along the first direction that is substantially perpendicular to the longitudinal direction. When the attachment tab 62 is inserted into the channel 40, the distal spacer head surface 50 can face or abut the proximal head body surface 30. The distal portion 43 of the channel 40 can be open to the proximal portion 41 of the channel 40 along the longitudinal direction. The attachment tab 62 can be disposed such that the spacer 24 defines a gap 64 that extends from the attachment tab 62 to the spacer head 46, and in particular to the distal spacer head surface 50, along the longitudinal direction. When the attachment member 58 is inserted into the channel 40, the gap 64 can receive a portion of the head body 26 that includes the proximal head body surface 30 and an opposed inner surface 66 that defines a proximal end of the distal portion 43 of the channel 40.

The attachment member 58 can further include a retention member 68 that can releasably secure to the radial trial implant 22. In particular, the retention member 68 can releasably secure to a complementary retention member of the head body 26 in the channel 40. In one example, the retention member 68 can be press-fit in the channel 40, and in particular in the distal portion 43 of the channel 43. The press-fit engagement can be removed when a sufficient force is applied to the spacer 24 along a second direction that is opposite the first direction, thereby causing the spacer 24 to be removed from the radial trial implant 22. The second direction can be referred to as a removal direction. The first direction can be referred to as an attachment direction.

Referring now to FIGS. 1 and 7, when the attachment member 58 is inserted into the channel 40 in the first direction, the spacer head 46 can face or abut the head body 26 of the trial radial implant 22. In particular, the distal spacer head surface 50 can face or abut the proximal head body surface 30. Thus, the orthopedic trial implant assembly 20 can define a composite head 70 that includes the head body 26 and the spacer head 46. The composite head 70 can define a proximal composite head surface 72 and a distal composite head surface 74 opposite the proximal composite head surface 72 along the longitudinal direction. In particular, the distal composite head surface 74 is spaced from the proximal composite head surface 72 substantially in the distal direction. Conversely, the proximal composite head surface 72 is spaced from the distal composite head surface 74 in the proximal direction.

The composite head 70 defines the composite head height 113 that extends from the proximal composite head surface 72 to the distal composite head surface 74 substantially along the longitudinal direction. One of the proximal composite head surface 72 and the distal composite head surface 74 is defined by the head body 26, and the other of the proximal composite head surface 72 and the distal composite head surface 74 is defined by the spacer head 46. In one example, the proximal spacer head surface 48 defines the proximal composite head surface 72, and the distal head body surface 32 defines the distal composite head surface 74. While the spacer head 46 is disposed proximal of the head body 26 in one example, it is envisioned that the spacer 24 can alternatively attach to the head body 26 such that the spacer head 46 is disposed distal of the head body 26. In this regard, the proximal spacer head surface 48 can face the distal head body surface 32. Further, the proximal head body surface 30 can define the proximal composite head surface 72, and the distal spacer head surface 50 can define the distal composite head surface 74.

Referring now to FIGS. 9A-9C, the orthopedic trial implant assembly 20 can include a plurality of spacers 24, such as a first spacer 24a and a second spacer 24b. Each of the plurality of spacers 20 can be selectively and removably attached to the radial trial implant 22. That is, each the spacers 24 can be attached to the radial trial implant 22 in the manner described above. Further, each of the spacers 24 can be removed from the radial trail implant in the manner described above.

The first spacer 24a can be attached to the radial trial implant 22 in the manner described above so as to define a first composite head 70a. The second spacer 24b can be attached to the radial trial implant 22 in the manner described above so as to define a second composite head 70b. Each of the spacers 24 of the plurality of spacers 24 can have different spacer heights substantially along the longitudinal direction as described above. For instance, the first spacer 24a can define a first spacer height HS1. Thus, when the first spacer 24a is attached to the radial trial implant 22 in the manner described above, the spacer head 46 of the first spacer 24a and the head body 26 can combine to define a first composite head 70a having a first composite head height. The first spacer 24a can be removed from the radial trial implant 22, and the second spacer 24b can be attached to the radial trail implant 22, such that the spacer head 46 of the second spacer 24b and the head body 26 can combine to define a second composite head 70b having a second composite head height. The second spacer 24b can define a second spacer height HS2 that is different than HS1. For instance, the second spacer height HS2 can be greater than the first spacer height HS1. Thus, the height of the resulting first composite head 70a can be different than the height of the resulting second composite head 70b. For instance, the height of the second composite head 70b can be greater than the height of the first composite head 70a. It is appreciated that the respective attachment members 58, including the extension members 60 and the attachment tabs 62, of the differently sized spacers 24 can be sized and shaped identical to each other, within manufacturing tolerances, such that the attachment members 58 can removably attach to the same radial trial implant 22.

Referring now to FIGS. 10A-10D, the orthopedic trial implant assembly 20 can be configured to identify a size of a permanent implant that is to be implanted in the proximal radius 44. The term "permanent" implant indicates that the implant is not intended to be removed prior to completion of the surgical procedure. In particular, as illustrated at FIG. 10B, the radial trial spacer 22 is coupled to the proximal radius. In particular, the stem 28 of the radial trial spacer 22 is inserted into the medullary canal of the proximal radius 44 such that the head body 26 is disposed in the gap 42. In some examples, the stem has been previously sized to fit into the medullary canal using a sounder that abuts the cortical bone in the medullary canal to determine the appropriate diameter or alternative cross-sectional dimension of the stem. In some examples, the stem can be sized to be loosely received in the medullary canal. When the head body 26 includes the cutting teeth 56 described above with respect to FIGS. 4B-4D, rotation of the radial trial spacer 22 about its central longitudinal axis can cause the cutting teeth to remove bone from the proximal radius, thereby planarizing the proximal radius. Thus, the head can be seated on a planar surface defined by the proximal radius. As illustrated in FIG. 10B, the head body 46 does not span the entirety of the gap 42 from the proximal radius 44 to the complementary articulating surface 47.

Thus, as illustrated in FIG. 10B, one of the radial trial spacers 24 having a known height can be selected. Because the height of the corresponding spacer head 46 is known, and the height of the head body 26 is known, the resulting height of the resulting composite head can be easily calculated. As shown in FIG. 10B, the first trial spacer 24a can be aligned with the radial trial implant 22, such that a sliding movement of the first trial spacer 24a in the first direction causes the first trial spacer 24a to be attached to the radial trial implant 22, as shown in FIG. 10C. However, in FIG. 10C, it is observed that the height of the first composite head 70a is less than the height of the gap 42 along the longitudinal direction. Thus, the first composite head 70a fails to extend from the proximal radius 44 to the complementary articulation surface 47 (see FIG. 10A).

Accordingly, referring to FIGS. 10C-D, the first trial spacer 24a can removed from the radial trial implant 22 by moving the first trial spacer 24a in the second direction with respect to the radial trial implant 22. Advantageously, the radial trial implant 22 can remain coupled to the proximal radius while the first trial spacer 24a is removed. Otherwise said, the first trial spacer 24a can be removed from the radial trail implant 22 without removing the radial trial implant 22 from the proximal radius 44.

Referring now to FIG. 10D in particular, once the first trial spacer 24a has been removed, the second trial spacer 24b can be attached to the radial trial implant 22 in the manner described above. Because the height of the corresponding spacer head 46 of the second trial spacer 24b is known, and the height of the head body 26 is known, the resulting height of the resulting second composite head 70b can be easily calculated. As illustrated in FIG. 10D, the second composite head 70 extends substantially from the proximal radius 74 to the opposed complementary articular surface 47 (see FIG. 10A). Thus, the height of the second composite head 70b is substantially equal to the height of the gap 72 along the longitudinal direction. Accordingly, referring now to FIG. 10E, a permanent radial implant 80 among a kit of permanent implants can be selected having a head height that is substantially equal to, or corresponding best to, the height of the second composite head 70b and therefore the height of the gap 72. Referring again to FIG. 10D, the second trial spacer 24 can be removed from the radial trial implant 22, and the radial trial implant can be removed from the proximal radius. Next, the selected permanent radial implant 80 can be selected and implanted in the proximal radius 74. In particular, a stem of the permanent radial implant 80 can be inserted into the medullary canal, and the head of the permanent radial implant 80 can articulate about the complementary articulating surface defined by one or both of the ulna and the distal humerus. The permanent radial implant 80 can be made from titanium, alloys thereof, stainless steel, alloys thereof, or any suitable biocompatible metal or other material.

It is recognized that different patients will have differently sized proximal radii. Therefore, a kit can be provided that includes a plurality of radial trial implants 22 (see FIG. 4A) that have different sizes and can be selected for implantation into an appropriately sized proximal radius. Further, each of the radial trial implants 22 can be configured to be removably attached to the same trial spacers. Thus, the radial trial implants 22 can have substantially identically sized channels that receive the trial spacers. The radial trail implants 22 can have at least one size or shape that is different from at least one other of the radial trial implants 22. For instance, the stems 28 can be sized differently from each other. In one example, the stems 28 of the radial trial implants 22 can define different cross-sectional dimensions so as to define the different sizes. The stems 28 can be cylindrical or tapered, and thus the cross-sectional dimensions can be defined by respective diameters of the stems. The cross-sectional dimensions are measured at a constant distance from the distal head body surface 32 in the distal direction.

Thus, at least some of the stems of the radial trial implants of the kit are cross-sectionally sized differently with respect to other stems of the radial trial implants of the kit along a direction that is substantially perpendicular to the longitudinal direction. For instance, at least some of the stems of the radial trial implants are cross-sectionally sized differently with respect to other stems of the radial trial implants in a plane that is oriented substantially perpendicular to the longitudinal direction. Further at least some of the head bodies of the radial trial implants of the kit can be cross-sectionally sized differently with respect to other head bodies of the radial trial implants of the kit along a direction that is substantially perpendicular to the longitudinal direction.

It is further envisioned that the kit can include a plurality of the spacers 24 having different spacer head heights as described above, Each of the spacers 24 of the kit can be configured to attach to each of the radial trial implants 22 of the kit. For instance, the attachment members 56 of the spacers 24 of the kit can all be substantially equally sized and shaped, and all of the slots 40 of the radial trial implants 22 of the kit can be substantially equally sized and shaped.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed:
1. An orthopedic trial implant assembly comprising:
at least one radial trial implant including:
a head body that defines a proximal head body surface and a distal head body surface opposite the proximal head body surface substantially along a longitudinal direction, and the head body has a head body height that extends from the proximal head body surface to the distal head body surface along the longitudinal direction; and
a stem that extends from the head body along a distal direction that is substantially defined by the longitudinal direction; and
at least one spacer that is configured to removably attach to the radial trial implant along a direction substantially perpendicular to the longitudinal direction so as to define a composite head including the head body and a spacer head of the spacer, wherein the composite head defines a proximal composite head surface and a distal composite head surface opposite the proximal composite head surface along the longitudinal direction, and the composite head defines a composite head height from the proximal composite head surface to the distal composite head surface,
wherein one of the proximal composite head surface and the distal composite head surface is defined by the head body, and the other of the proximal composite head surface and the distal composite head surface is defined by the spacer head,
wherein the composite head height is greater than the head body height,
wherein the at least one spacer comprises an attachment member that extends from the spacer head and is configured to be removably received by the head body so as to removably attach the at least one spacer to the at least one radial trial implant, and
wherein the distal head body surface defines a plurality of cutting teeth configured to planarize the radius as the head body is rotated about its central axis that is oriented along the longitudinal direction.
2. The orthopedic trial implant assembly of claim 1, wherein the spacer head defines a proximal spacer head surface and a distal spacer head surface opposite the proximal spacer head surface along the longitudinal direction, the proximal spacer head surface defines the proximal composite head surface, and the head body defines the distal composite head surface.
3. The orthopedic trial implant assembly of claim 2, wherein the at least one spacer defines a spacer height from the proximal spacer head surface to the distal spacer head surface along the longitudinal direction, and the at least one spacer height is less than the height of the head body.
4. The orthopedic trial implant assembly of claim 2, wherein the at least one spacer comprises a plurality of spacers that each have different respective spacer heights, and each of the spacers is configured to be removably attached, selectively, to the radial trial implant so as to define corresponding different composite head heights.

5. The orthopedic trial implant assembly of claim 4, wherein each spacer of the plurality of spacers comprises an attachment tab that is configured to be received, selectively, in a channel of the radial trial implant so as to attach the spacer to the radial trial implant, and all tabs are substantially identically sized and shaped.

6. The orthopedic trial implant assembly of claim 1, wherein the radial trial implant defines a channel that extends into the head body and is configured to receive the attachment member of the at least one spacer so as to removably attach the at least one spacer to the at least one radial trial implant.

7. The orthopedic trial implant assembly of claim 6, wherein the head body comprises a side wall that extends from the proximal head body surface and the distal head body surface, and the channel extends into the side wall along the direction substantially perpendicular to the longitudinal direction.

8. The orthopedic trial implant assembly of claim 6, wherein the attachment member comprises:
an extension member having a first end that extends out from the distal spacer head surface, and the extension member extends from the first end to a second end substantially along the longitudinal direction; and
an attachment tab that extends from the second end of the extension member substantially along a direction perpendicular to the longitudinal direction and is configured to be inserted into the channel such that the distal spacer head surface faces the proximal head body surface.

9. The orthopedic trial implant assembly of claim 1, wherein the cutting teeth are circumferentially spaced from each other about the distal head body surface.

10. The orthopedic trial implant assembly of claim 1, wherein the cutting teeth are oriented straight and linear.

11. The orthopedic trial implant assembly of claim 1, wherein the cutting teeth define a swept spiral shape.

12. The orthopedic trial implant assembly of claim 1, wherein the at least one radial trial implant comprises a plurality of radial trial implants that are each configured to be removably attached, selectively, to the at least one spacer, wherein the stems of the radial trial implants are differently sized from each other.

13. The orthopedic trial implant assembly of claim 12, wherein the stems define different cross-sectional dimensions so as to define respective different sizes.

14. The orthopedic trial implant assembly of claim 13, wherein the cross-sectional dimensions are defined by respective diameters of the stems.

15. The orthopedic trial implant assembly of claim 1, wherein the head body is a single unitary structure.

16. The orthopedic trial implant assembly of claim 1, wherein the head body surface defines a concave surface.

17. The orthopedic trial implant assembly of claim 16, wherein the head body defines an articular concave surface configured to cooperate with a humerus or humeral prosthesis to provide radiohumeral joint articulation.

18. The orthopedic trial implant assembly of claim 1, wherein the stem extends from the distal composite head surface.

* * * * *